United States Patent [19]

Preissman

[11] Patent Number: 5,476,465

[45] Date of Patent: Dec. 19, 1995

[54] SURGICAL CABLE CRIMP

[75] Inventor: Howard E. Preissman, Dallas, Tex.

[73] Assignee: AMEI Technologies Inc., Wilmington, Del.

[21] Appl. No.: 253,200

[22] Filed: Jun. 1, 1994

Related U.S. Application Data

[63] Continuation of Ser. No. 52,059, Apr. 21, 1993, abandoned.

[51] Int. Cl.⁶ .................................................. A61B 17/88
[52] U.S. Cl. .............................................. 606/61; 606/74
[58] Field of Search ........................... 606/232, 61, 151, 606/157, 158, 74; 24/20 R, 20 W, 23 W, 25, 268, 689

[56] References Cited

U.S. PATENT DOCUMENTS

| | | |
|---|---|---|
| 409,327 | 8/1889 | Maeurer . |
| 409,721 | 8/1889 | Williams, Jr. . |
| 1,234,435 | 7/1917 | Wood . |
| 1,258,580 | 3/1918 | Lassiter . |
| 1,304,620 | 5/1919 | Steinkoenig . |
| 1,346,940 | 7/1920 | Collins . |
| 1,347,579 | 7/1920 | Henrikson . |
| 1,388,716 | 8/1921 | Hughes . |
| 1,562,568 | 11/1925 | Linquist . |
| 1,641,077 | 8/1927 | Fouquet . |
| 1,647,398 | 11/1927 | Draheim et al. . |
| 1,717,766 | 6/1929 | Eimler . |
| 2,049,361 | 7/1936 | Ericsson . |
| 2,279,068 | 4/1942 | Sierbrandt ............................ 140/121 |
| 2,291,413 | 7/1942 | Sierbrandt . |
| 2,455,609 | 12/1948 | Scheib . |
| 2,509,290 | 5/1950 | Elvin et al. ............................ 288/17 |
| 2,883,096 | 4/1959 | Dawson ................................ 223/102 |
| 2,928,395 | 3/1960 | Forbes et al. . |
| 3,035,476 | 5/1962 | Fogden .................................... 87/9 |
| 3,035,583 | 5/1962 | Hirsch et al. . |
| 3,078,755 | 2/1963 | Chace, Jr. ................................ 87/9 |
| 3,111,945 | 11/1963 | Von Solbrig . |

(List continued on next page.)

FOREIGN PATENT DOCUMENTS

| | | |
|---|---|---|
| 218602 | 9/1956 | Australia . |
| 1158422 | 12/1983 | Canada . |
| 0019062 | 11/1980 | European Pat. Off. . |
| 0117981 | 9/1984 | European Pat. Off. . |
| 348272A | 12/1989 | European Pat. Off. . |
| 999646 | 2/1952 | France . |
| 123046 | 10/1926 | Germany . |
| 1177769 | 9/1964 | Germany . |
| 1958429 | 7/1971 | Germany . |
| 3146634 | 6/1983 | Germany . |
| 3517204 | 11/1986 | Germany . |
| 275268 | 8/1951 | Switzerland . |
| 506401 | 5/1976 | U.S.S.R. . |
| 163340 | 6/1921 | United Kingdom . |
| 579288 | 7/1946 | United Kingdom . |
| 727988 | 4/1955 | United Kingdom . |

(List continued on next page.)

OTHER PUBLICATIONS

Danek Medical, Inc. ©1994, "DANEK® Titanium Cable System" (LIT-SONG-TSS-93) (two pages).

Danek Medical, Inc. ©1994, "DANEK® Cable Instruments" (LIT-DC1-94) (two pages).

Danek Group, Inc., Medical Division, "A Flexible Reminder to Swtich to the SONGER™ Cable System."

Primary Examiner—Tamara L. Graysay
Attorney, Agent, or Firm—Baker & Botts

[57] ABSTRACT

A surgical cable crimp is disclosed for securing a surgical cable in a loop. The crimp has a crimp body with a head and a neck. The crimp body has a first longitudinal bore formed therein. The head has a second bore extending through the head and offset from the first longitudinal bore. The second bore is sized to allow a surgical cable with a ball end termination to pass therethrough until the ball end termination reaches the second bore. The surgical cable may then be looped about a selected portion of the patient's body and then inserted into the first bore, and then the neck is crimped to secure the surgical cable in the first bore and thereby form a secured loop.

1 Claim, 3 Drawing Sheets

U.S. PATENT DOCUMENTS

| | | | |
|---|---|---|---|
| 3,125,095 | 3/1964 | Kaufman et al. . | |
| 3,215,768 | 11/1965 | Murphy | 174/36 |
| 3,233,800 | 2/1966 | Catania | 223/102 |
| 3,323,208 | 6/1967 | Hurley, Jr. | 30/124 |
| 3,344,452 | 10/1967 | Quimby | 14/21 |
| 3,507,270 | 4/1970 | Ferrier . | |
| 3,587,585 | 6/1971 | Ceravolo . | |
| 3,636,956 | 1/1972 | Schneider . | |
| 3,762,418 | 10/1973 | Wasson . | |
| 3,802,438 | 4/1974 | Wolvek | 606/232 |
| 3,879,147 | 4/1975 | Morell | 403/369 |
| 3,892,241 | 7/1975 | Leveen | 248/67.5 |
| 3,910,281 | 10/1975 | Kletschka et al. . | |
| 3,952,377 | 4/1976 | Morell | 24/136 |
| 3,965,541 | 6/1976 | Davison | 24/115 |
| 3,976,079 | 8/1976 | Samuels et al. . | |
| 3,993,109 | 11/1976 | Fortsch | 140/123.6 |
| 3,997,138 | 12/1976 | Crock et al. | 248/67.5 |
| 4,047,533 | 9/1977 | Perciaccante et al. . | |
| 4,050,464 | 9/1977 | Hall . | |
| 4,084,625 | 4/1978 | Brinegar | 140/123.5 |
| 4,128,100 | 12/1978 | Wendorff . | |
| 4,200,126 | 4/1980 | Fish | 138/133 |
| 4,283,933 | 8/1981 | Wiener | 72/409 |
| 4,291,698 | 9/1981 | Fuch et al. . | |
| 4,333,649 | 6/1982 | Vaughn et al. | 273/73 |
| 4,387,489 | 6/1983 | Dudek | 24/133 |
| 4,412,474 | 11/1983 | Hara | 87/6 |
| 4,509,233 | 4/1985 | Shaw | 24/136 |
| 4,527,554 | 7/1985 | Klein . | |
| 4,570,618 | 2/1986 | Wu | 606/61 |
| 4,587,963 | 5/1986 | Leibinger et al. . | |
| 4,592,355 | 6/1986 | Antebi . | |
| 4,625,717 | 12/1986 | Covitz . | |
| 4,643,178 | 2/1987 | Nastari et al. . | |
| 4,712,770 | 12/1987 | Wiederkehr | 254/98 |
| 4,716,630 | 1/1988 | Skyba | 24/134 |
| 4,716,886 | 1/1988 | Schulman et al. . | |
| 4,741,330 | 5/1988 | Hayhurst | 128/92 |
| 4,750,492 | 6/1988 | Jacobs . | |
| 4,773,402 | 9/1988 | Asher et al. . | |
| 4,790,303 | 12/1988 | Steffee . | |
| 4,889,110 | 12/1989 | Galline et al. | 606/69 |
| 4,889,320 | 12/1989 | Pasbrig | 254/252 |
| 4,901,721 | 2/1990 | Hakki | 606/103 |
| 4,946,462 | 8/1990 | Watanabe | 606/148 |
| 4,946,467 | 8/1990 | Ohi et al. | 606/228 |
| 4,959,069 | 9/1990 | Brennan et al. | 606/228 |
| 4,966,600 | 10/1990 | Songer et al. | 606/74 |
| 4,969,895 | 11/1990 | McLeod et al. | 606/96 |
| 5,010,145 | 4/1991 | Ikada et al. | 525/415 |
| 5,015,023 | 5/1991 | Hall | 294/102.1 |
| 5,019,093 | 5/1991 | Kaplan et al. | 606/228 |
| 5,052,094 | 10/1991 | Plasse et al. | 29/252 |
| 5,057,113 | 10/1991 | Mingozzi | 606/103 |
| 5,059,207 | 10/1991 | Shah | 606/223 |
| 5,062,184 | 11/1991 | Rowland | 24/16 |
| 5,089,012 | 2/1992 | Prou | 606/224 |
| 5,092,868 | 3/1992 | Mehdian | 606/74 |
| 5,092,889 | 3/1992 | Campbell, Jr. | 623/16 |
| 5,116,340 | 5/1992 | Songer et al. | 606/103 |
| 5,127,144 | 7/1992 | Plasse et al. | 29/252 |
| 5,133,738 | 7/1992 | Korthoff et al. | 606/224 |
| 5,199,146 | 4/1993 | Grover et al. | 29/268 |
| 5,224,946 | 6/1993 | Hayhurst et al. | 606/72 |
| 5,318,575 | 6/1994 | Chesterfield et al. | 606/151 |
| 5,395,374 | 3/1995 | Miller et al. | 606/74 |

FOREIGN PATENT DOCUMENTS

| | | |
|---|---|---|
| 958284 | 5/1964 | United Kingdom . |
| 1550186 | 8/1979 | United Kingdom . |
| 2146535 | 4/1985 | United Kingdom . |

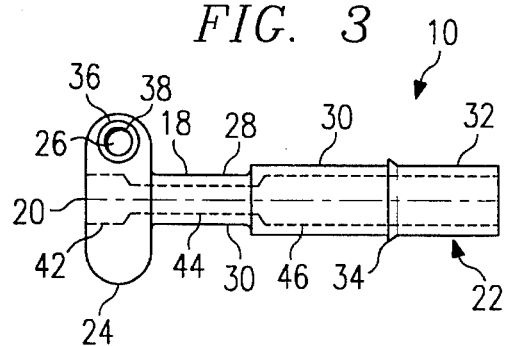
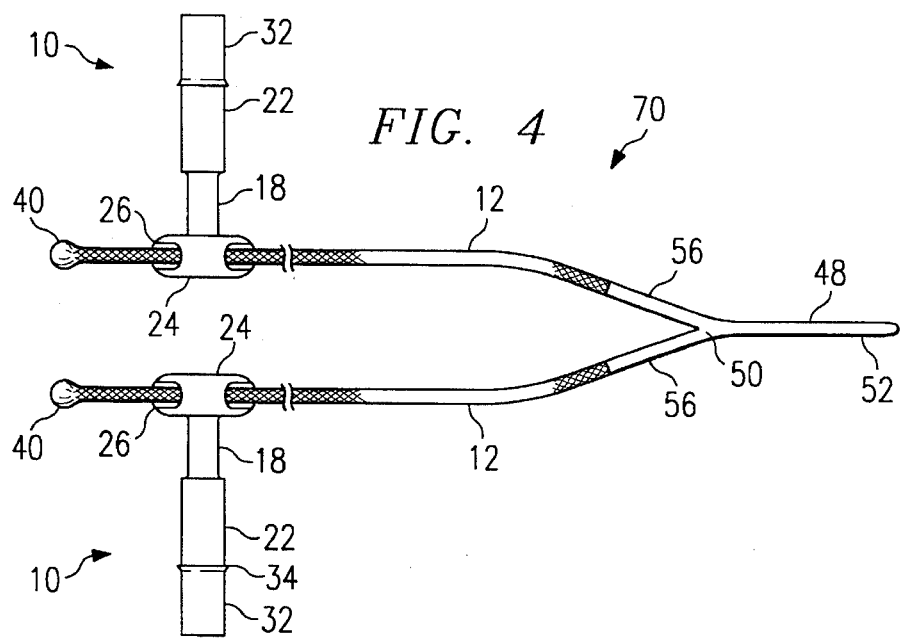
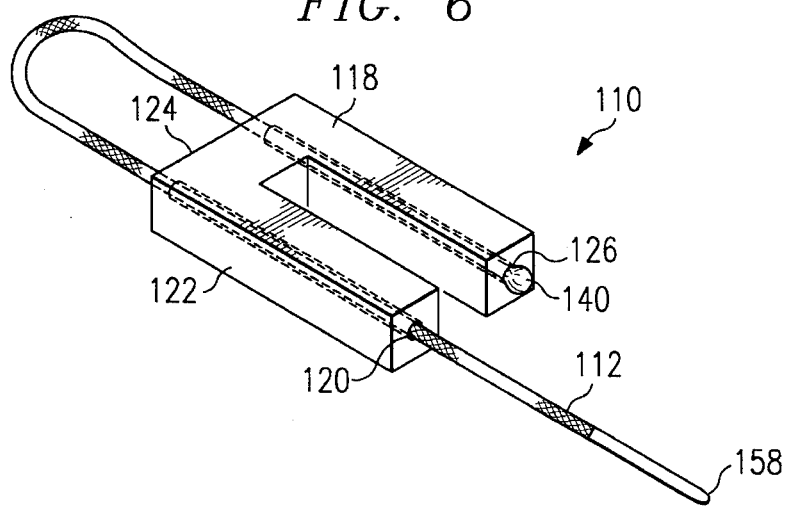

SURGICAL CABLE CRIMP

This application is a continuation of U.S. application Ser. No. 08/052,059 filed Apr. 21, 1993, entitled "Surgical Cable Crimp" by Howard E. Preissman, now abandoned.

RELATED APPLICATIONS

This application is related to copending U.S. patent application Ser. No. 08/052,191 filed Apr. 21, 1993, entitled Surgical Cable Leader and Terminations (Attorney Docket 909280205); copending U.S. patent application Ser. No. 08/052,058 filed Apr. 21, 1993, entitled Orthopedic Cable Tensioner (Attorney Docket 90928-0204); U.S. patent application Ser. No. 08/051,179 filed Apr. 21, 1993, entitled Surgical Cable and Cable Clamp (Attorney Docket 90928-0181, now abandoned); and copending U.S. patent application Ser. No. 08/230,196 filed Apr. 20, 1994, entitled Surgical Cableand Cable Clamp (Attorney Docket 90928-0251).

TECHNICAL FIELD OF THE INVENTION

This invention relates to surgically implanted wires and cables, and more particularly, relates to improved methods and apparatus for use in surgically installing wires and cables at selected locations in a patient's body.

BACKGROUND OF THE INVENTION

Surgical wires and cables are used in a variety of surgical procedures, for example, reconstructive spine surgery such as fusions, spine trauma surgery, total hip arthroplasty, fracture fixation, open heart surgery for closures of the sternum, oral and facial surgery to fix mandibular fractures and the like, and other surgical procedures. Often, surgical cables and wires are used to encircle or loop about bones to hold them together for healing or fusion in some types of spinal surgery. For purposes of this application, "cable" includes monofilament and single strand wire along with multifilament and multistrand cable and wire ropes.

In some orthopedic procedures, it is desirable to provide a tensile force to selected portions of a patient's body such as two adjacent vertebrae. This is frequently accomplished by placing two loops formed of surgical cable about the vertebrae. In placing the loops, it is necessary to pass the cables under the lamina of the vertebrae (sublamina) to establish the desired tension in the cables, and then to attach the cables in loops. One method of accomplishing these tasks is for the surgeon to secure a suture to a midsection of a cable, pass the cable sublamina, and then cut the suture and cable so that two cables exist under the lamina of the patient. The cables can then be looped about the vertebrae and tightened by hand with surgeon plucking the cables to determine tension. After tightening, the surgeon secures the cables in their respective loops.

One method of securing the cables in their respective loops is to provide a permanent loop on one end of the cables. This method is accomplished by forming a small loop on one end of the cable and securing the small loop with a crimp, and then passing the end opposite the small loop through the small loop in an arrangement similar to a cowboy's lasso. Then a crimp member with a flange may be placed on the cable opposite the small loop end and slid along the cable until snug against the small loop member. Then after applying the desired tension, the crimp member may be crimped so that a secured loop is formed. This method involves two crimp members and has two parts of the cable resting against each other which may lead to increased wear of the cable and an increased likelihood of premature failure.

Another method is to provide a bar member with two transverse apertures. A stop member is attached to one end of the cable and then the other cable end is passed through one of the apertures until the stop rests against the bar member. The cable end opposite the stop member forms a loop and is then passed through the other aperture and then through a crimp member. The crimp member is placed snugly against the bar member and crimped once the desired tension is applied to the cable. Among the shortcomings of this method may be the difficulty in holding all the parts with surgical instruments during the procedure. Additionally, this method and the previously described method do not protect against fraying once the cable is cut. See U.S. Pat. No. 5,116,340, which is incorporated by reference for all purposes.

Therefore, a need has arisen for a surgical cable crimp that efficiently secures a surgical cable in a loop, uses a small number of parts, is easily handled by surgical instruments, does not allow the cable to rest against other portions of the cable, and helps prevent fraying.

SUMMARY OF THE INVENTION

In accordance with the present invention, the disadvantages and problems associated with previously available surgical cables and their associated crimps or fasteners have been substantially reduced or eliminated by use of the present invention. The present invention includes components and methodologies for applying support to selected portions of a patient's body.

In accordance with the present invention a cable crimp is provided with a crimp body having a first longitudinal bore extending through the crimp body. A head with the longitudinal bore extending therethrough, is secured to or formed as one end of the crimp body. The head has a second bore extending therethrough and offset from the first longitudinal bore. The second bore holds one end of a surgical cable having an enlarged termination while the other end of the surgical cable is passed through the longitudinal bore. A portion of the crimp body may then be crimped to secure the cable in a loop.

In accordance with another aspect of the present invention, a method is provided for securing a surgical cable in a loop about a selected region of a patient's body.

An important technical advantage of the present invention includes providing a cable crimp which will prevent fraying of the end of a surgical cable secured in a loop by the cable crimp. Another important technical advantage of the present invention includes providing a surgical crimp that readily cooperates with surgical instruments.

BRIEF DESCRIPTION OF THE DRAWINGS

For a more complete understanding of the present invention, and the advantages thereof, reference is now made to the following description taken in conjunction with the accompanying drawings, in which:

FIG. 3 is an elevational view of one aspect of the present invention showing one embodiment of the surgical cable crimp;

FIG. 4 is a top schematic view of one aspect of the present invention showing another embodiment of the surgical cable crimp being used with a surgical cable;

FIG. 6 is an isometric view of the present invention showing another embodiment of the present invention.

DETAILED DESCRIPTION OF THE INVENTION

The preferred embodiments of the present invention and its advantages are best understood by referring to FIGS. 1 through 6 of the drawings, like numerals being used for like and corresponding parts of the various drawings.

Figure 1:
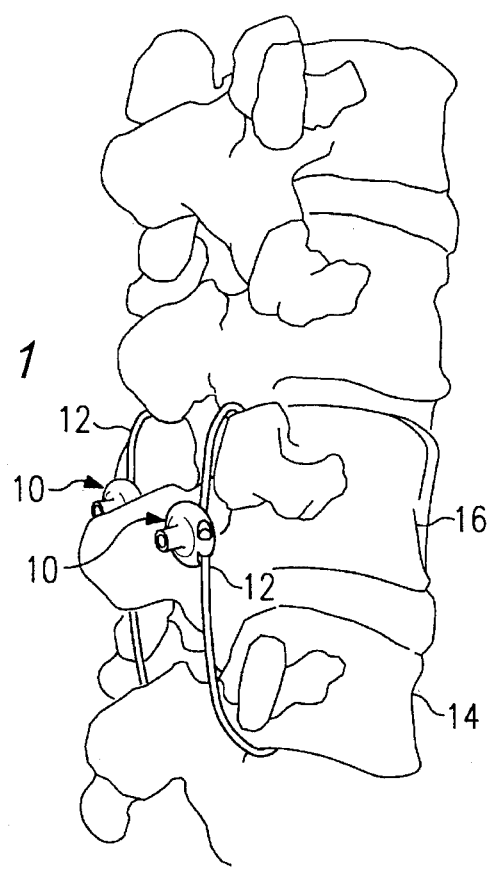
FIG. 1 is a schematic view of one aspect of the present invention showing one embodiment of the surgical cable crimp securing a surgical cable in a loop about a patient's vertebrae.

One aspect of the present invention relates to surgical cable crimps 10 (FIG. 1) for applying support to selected portions of a patient's body. Crimps 10 are preferably used in conjunction with surgical cable 12. Crimps 10 may also be used in conjunction with various types of surgical cables such as cable 70 shown in FIG. 4, a leader 48 (FIG. 4) and with various surgical tools such as cable tensioner 54 shown in FIG. 5. Referring to FIG. 1, there is shown two crimps 10 of the present invention securing two loops formed by surgical cable 12 about vertebrae 14 and 16 of a patient's spine. Crimps 10 are secured to cables 12 to hold the cables in a secured loop once the desired tension has been placed on respective cables 12.

Cable 12 may be a multifilament cable. Cable 12 may also be a monofilament cable or a braided cable, which is formed from layers of woven strands. Additionally, cable 12 may be a 7×7×19 LANG LAY wire rope. Cable 12 may be formed from titanium, e.g., titanium 6A14V of specification F136 of the American Society of Testing Material. Alternatively, cable 12 may be formed from MP35N of Specification F562 of the American Society of Testing Material, stainless steel, or ultra high molecular weight polyethylene (UHMW-PE).

Figure 2:
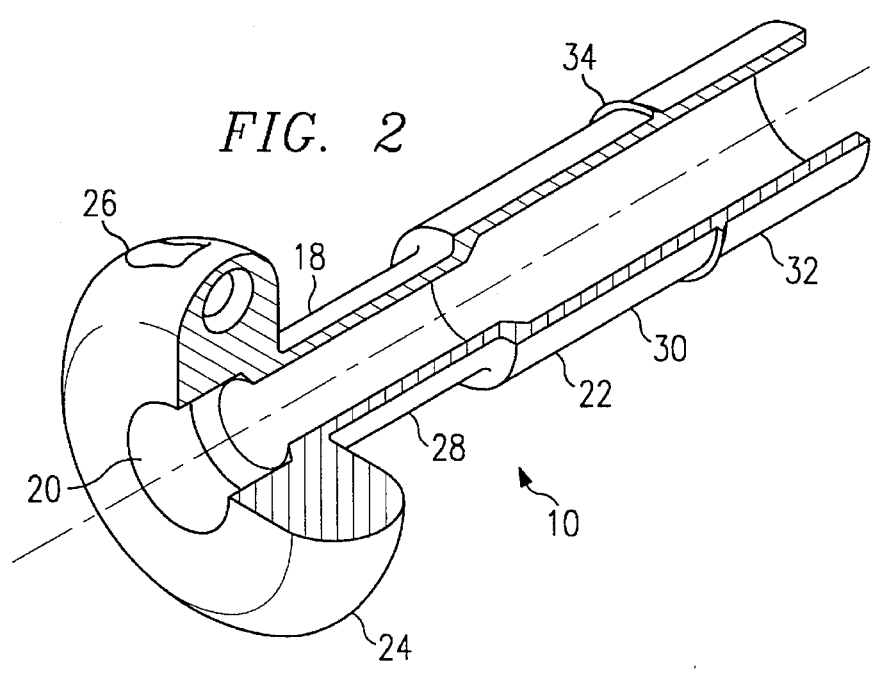
FIG. 2 is an isometric drawing in section of the present invention showing one embodiment of the surgical cable crimp.

Referring now to FIG. 2, there is shown crimp 10 that is formed by crimp body 18 and crimp head 24. First longitudinal bore or channel 20 extends through crimp body 18 and head 24. Crimp 10 has neck 22 that may be formed as one integral part of crimp body 18 or attached to crimp body 18. Also formed as an integral part of crimp body 18, or attached to crimp body 18, is crimp head 24.

Crimp head 24 has a second bore or channel 26 extending through a portion of head 24 and offset from first longitudinal bore 20. Crimp 10 is preferably formed of titanium, but may also be formed of MP35N of Specification 562 of the American Society of Testing Materials, stainless steel, or ultra high molecular weight polyethylene.

Neck 22 may have several sections with varying outside diameters, e.g., 28, 30, and 32. Additionally, neck 22 may have a shoulder 34 to facilitate the attachment of surgical instruments to crimp body 18 to hold crimp 10 during surgery. When surgical cable 12 is passed through first longitudinal bore 20 and the desired tension has been applied to cable 12, neck 22 of crimp body 18 may be crimped, or plastically deformed, about cable 12 by applying a crimping force that may be generated by surgical pliers or a similar crimping tool so as to cause crimp 10 to hold and secure cable 12 by frictional forces developed between crimped neck 22 and the adjacent portion of cable 12. Neck 22 may be crimped or deformed on neck section 28. After crimping crimp 10, neck 22 also provides a convenient place to cut cable 12 and crimp 10. Neck 22 will then help prevent fraying of cable 12.

Referring now to FIG. 3, there is shown an elevational view of crimp 10. Crimp 10 has first longitudinal bore 20 that extends through crimp body 18 and head 24. Second bore 26 extends through a portion of head 24, and may have a first diameter 36 and a second diameter 38. First diameter 36 may have a diameter larger than the diameter of an enlarged cable termination such as ball termination 40 of cable 12 (see FIG. 4). Second diameter 38 may be sized to have a diameter smaller than the diameter of ball termination 40 of cable 12. First and second diameters 36 and 38 are thus sized to allow ball termination 40 to pass into first diameter section 36 of second bore 26, but not through second diameter section 38 of second bore 26. First longitudinal bore 20 may also be sized to have sections of varying inside diameters, but with a minimum inside diameter larger than the outside diameter of cable 12. For example, first longitudinal bore 20 may have a first inside diameter section 42 (shown in hidden lines), second inside diameter section 44, and third inside diameter section 46.

Surgical cable crimps 10 may be used with various types of surgical cables such as surgical cable assembly 70 shown in FIG. 4. Surgical cable assembly 70 includes two surgical cables 12 with each cable 12 passing through second bore 26 of its respective crimp 10. Cables 12 are joined by cable leader or cable guide 48. Cable leader 48 may be formed by attaching the ends of cable 12 at an attachment area or fork 50. Attachment area 50 may have a monofilament stem 52 extending from attachment area 50. In forming the configurations shown in FIG. 4, the ends of cable 12 opposite ball terminations 40 are threaded or passed through second bores 26 and then joined with attachment area 50.

Figure 5:
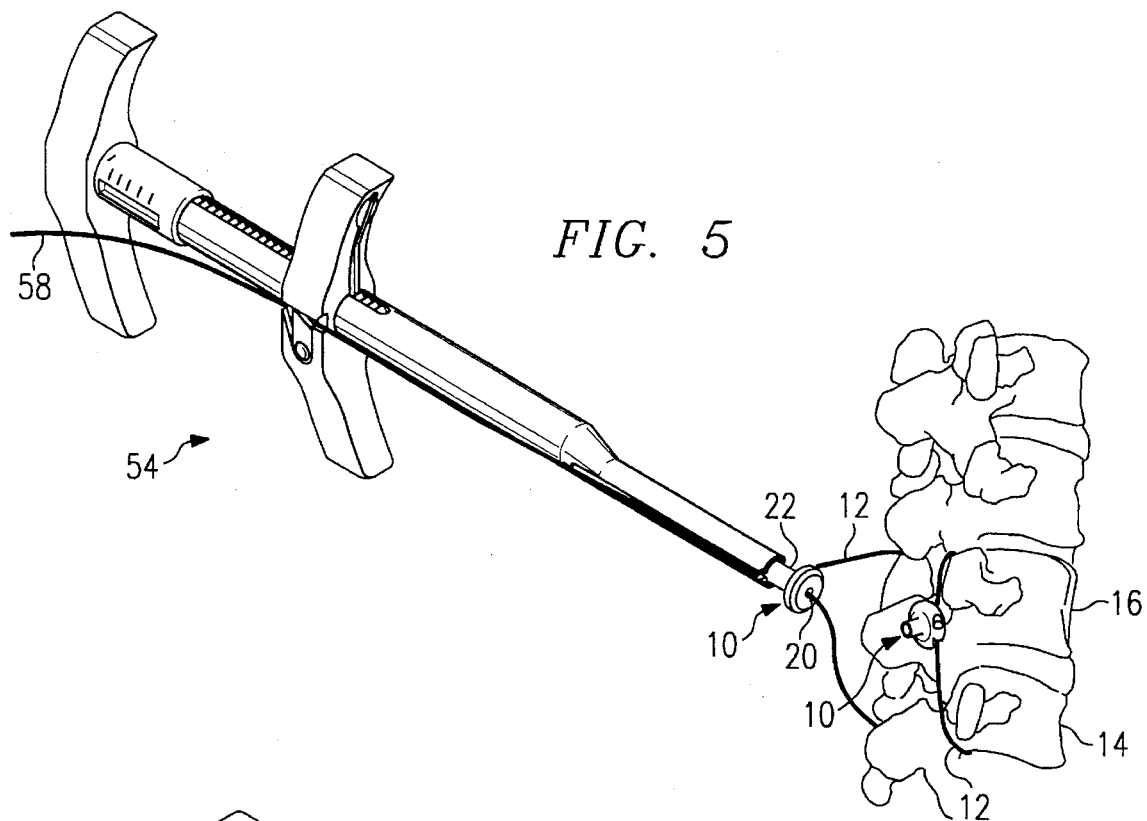
FIG. 5 is a schematic view of one aspect of the present invention showing another embodiment of the surgical cable crimp being used with a tensioner to apply a surgical loop about two vertebrae of a patient.

Referring now to FIG. 5, tensioner 54 is shown attached to crimp 10. Tensioner 54 may grip crimp 10 on neck 22, and in particular, neck section 32 and shoulder 34 (see FIG. 3). Tensioner 54 leaves neck section 28 of neck 22 available to be accessed by a surgical instrument, such as crimping pliers, so that neck 22 may be crimped after the desired tension has been applied to cable 12. After crimping section 28 of neck 22, neck 22 may be cut on section 28.

In operation, cables 12 are passed through second bores 26 of crimp 10 and then joined at attachment area 50 as previously described in connection with FIG. 4. Attachment area 50 or leader 48 with stem 52 may then be passed under the lamina of the patient's vertebrae so that two cables 12 are passed under the lamina of the patient. After passing the two cables 12 under the lamina of vertebrae 14 and 16, cable assembly 70 may be cut about section 56 (FIG. 4) to create two separate surgical cables 12 running under the lamina. Cables 12 may then be secured in a loop by their respective crimps 10.

Cable 12 is secured in a loop with its respective crimp 10 by passing cable end 58, which was created when cable assembly 70 was cut at section 56, through first longitudinal bore 20 of crimp 10. The desired tension is then applied to cable 12 by tensioner 54 so that ball termination 40 rests snugly against second bore 26 and cable 12 forms a loop about the patient's vertebrae with the desired tension. At this point, neck 22 is crimped or plastically deformed at neck section 28. Cable 12 is now in a secured loop. Cable 12 and crimp 10 may now be cut on neck 22.

Figure 5A:
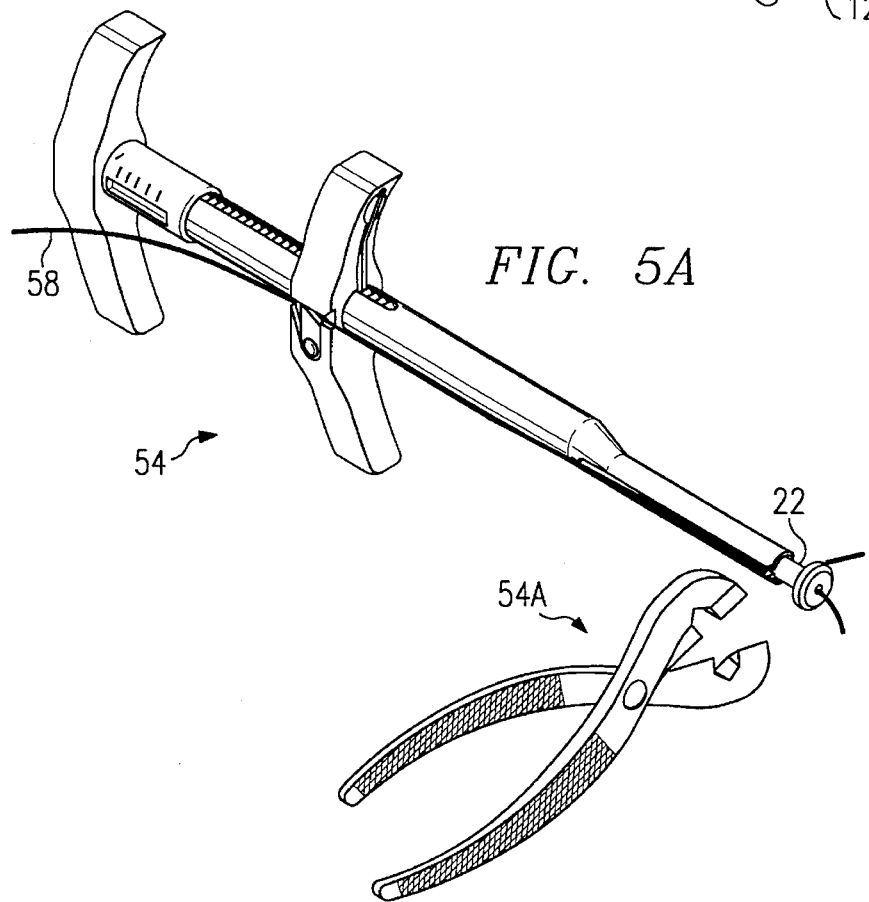
FIG. 5A is a schematic view of one aspect of the present invention showing the surgical cable crimp of FIG. 5 being used with a tensioner and showing crimp pliers that may be used with the cable crimp.

In applying the desired tension to the loop of cable 12, tensioner 54 may be used. See FIG. 5. To use tensioner 54, tensioner 54 grips crimp 10 on neck 22 about section 32 and shoulder 34. Then cable end 58 is threaded through first longitudinal bore 20 as previously described. Cable 12 that exits neck 22 farthest from crimp head 24 is then attached to a portion of tensioner 54 so that the desired tension may be applied. Tensioner 54 leaves first section 28 of crimp 10 exposed so that crimp pliers or other surgical instruments, e.g. crimping pliers 54A (FIG. 5A), may be used to crimp neck 22 and thereby secure cable 12 in a loop. Neck 22 may then be cut by any means known in the art. After applying the two loops as described, crimps 10 and cables 12 will define two secured loops about vertebrae 14 and 16 as shown in FIG. 1.

FIG. 6 shows an alternative embodiment of a surgical crimp 110. Crimp body 118 has a first longitudinal bore 120 and a second bore 126 which is offset from first bore 120. A portion of crimp body 118 containing first bore 120 and the portion of crimp body 118 containing second bore 126 are connected by head 124. First end 158 of cable 112 is inserted in second bore 126 until it exits the bore 126 proximate head 124, and then cable 112 is made to form a loop about the selected region of the patient's body and is then inserted into first longitudinal bore 120 proximate head 124. Cable 112 is then passed through first longitudinal bore 120 until exiting bore 120 opposite head 124. Neck 122 may then be crimped, and if desired cut by means known in the art. Thus a secured loop of cable 112 is formed.

Although the present invention and its advantages have been described in detail, it should be understood that various changes, substitutions, and alterations can be made therein without departing from the spirit and scope of the invention.

What is claimed is:

1. A method of forming a pair of loops about selected vertebrae of a patient's spine using surgical cables having a ball end and crimps having a first longitudinal bore and a second bore, comprising:

threading a leading end of a first surgical cable through the second bore of a first crimp;

threading a leading end of a second surgical cable through the second bore of a second crimp;

attaching the leading ends of the first and second surgical cables so that the attached ends may be guided through a selected region of the patient's spine;

passing the attached ends of the first and second surgical cable through the sublamina region of a vertebra while keeping the crimps near the ball ends of the surgical cables and above the sublamina region;

cutting the attached region of the surgical cables to form two unattached surgical cables passing sublamina the vertebra;

threading the leading end of the first surgical cable through the first longitudinal bore of the first crimp to form a loop with the desired tension;

applying a force to the neck of the first crimp to plastically deform the neck about the first surgical cable passing therethrough thereby securing the first surgical cable in a loop;

threading the leading end of the second surgical cable through the first longitudinal bore of the second crimp to form a loop with the desired tension; and applying a force to the neck of the second crimp to plastically deform the neck about the second surgical cable passing therethrough thereby securing the second surgical cable in a loop.

\* \* \* \* \*